United States Patent
Fishler et al.

(10) Patent No.: US 11,766,570 B2
(45) Date of Patent: *Sep. 26, 2023

(54) MANAGING COMMUNICATION INTERFERENCE IN LEADLESS DUAL-CHAMBER PACING SYSTEMS AND OTHER IMD SYSTEMS

(71) Applicant: Pacesetter, Inc., Sylmar, CA (US)

(72) Inventors: Matthew G Fishler, Scotts Valley, CA (US); Benjamin T. Persson, Saratoga, CA (US); Suresh Gurunathan, Palo Alto, CA (US)

(73) Assignee: Pacesetter, Inc., Sylmar, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 17/380,307

(22) Filed: Jul. 20, 2021

(65) Prior Publication Data

US 2021/0346707 A1 Nov. 11, 2021

Related U.S. Application Data

(63) Continuation of application No. 16/819,690, filed on Mar. 16, 2020, now Pat. No. 11,097,112, which is a (Continued)

(51) Int. Cl.
*A61N 1/372* (2006.01)
*A61B 5/00* (2006.01)
*G16H 40/60* (2018.01)

(52) U.S. Cl.
CPC ........ *A61N 1/37254* (2017.08); *A61B 5/0031* (2013.01); *A61N 1/37258* (2013.01); *G16H 40/60* (2018.01)

(58) Field of Classification Search
CPC ........... A61N 1/37254; A61N 1/37258; G16H 40/60; A61B 5/0031
See application file for complete search history.

(56) References Cited

U.S. PATENT DOCUMENTS 8,386,049 B2 2/2013 Persson et al.
8,554,333 B2 10/2013 Wu et al.
(Continued)

OTHER PUBLICATIONS

Notice of Allowance dated Jan. 24, 2020, U.S. Appl. No. 15/976,788, filed May 10, 2018.
(Continued)

*Primary Examiner* — Hee K Song
(74) *Attorney, Agent, or Firm* — Vierra Magen Marcus LLP

(57) ABSTRACT

Embodiments described herein relate to implantable medical devices (IMDs) and methods for use therewith. Such a method includes, during each of a plurality of message alert periods during which a communication capability of the IMD is enabled, determining whether a valid message is detected. In response to determining that no valid message was detected during a message alert period, the communication capability of the IMD is temporarily disable for a disable period. A length of the disable period may be increased in response to no valid message being detected during two consecutive message alert periods. A length of the disable period may be dependent on an operational mode of the IMD, such that the length of the disable period differs for different operational modes. The IMD may also enter a noise state, and remain in the noise state until the IMD receives a specified number of valid messages.

20 Claims, 7 Drawing Sheets

Related U.S. Application Data continuation of application No. 15/976,788, filed on May 10, 2018, now Pat. No. 10,632,315.

(56) References Cited

U.S. PATENT DOCUMENTS

| | | |
|---|---|---|
| 9,457,193 B2 | 10/2016 | Klimovitch et al. |
| 9,522,280 B2 | 12/2016 | Fishler et al. |
| 9,561,382 B2 | 2/2017 | Persson et al. |
| 10,632,315 B2 | 4/2020 | Fishler et al. |
| 2007/0150028 A1 | 6/2007 | Parkinson et al. |
| 2010/0023085 A1 | 1/2010 | Wu et al. |
| 2016/0121128 A1 | 5/2016 | Fishler et al. |
| 2016/0121129 A1 | 5/2016 | Persson et al. |
| 2017/0216610 A1* | 8/2017 | Yoder ................ A61N 1/37276 |
| 2018/0207433 A1 | 7/2018 | Koop et al. |
| 2019/0344088 A1 | 11/2019 | Fishler et al. |

OTHER PUBLICATIONS

U.S. Appl. No. 15/413,820, titled Mitigating Excessive Wakeups in Leadless Dual-Chamber Pacing Systems and Other Imd Systems Field of Technology, filed Jan. 24, 2017.

U.S. Appl. No. 15/423,404, titled Mitigating False Messaging in Leadless Dual-Chamber Pacing Systems and Other Imd Systems, filed Feb. 2, 2017.

U.S. Appl. No. 15/423,409, titled Mitigating False Messaging in Leadless Dual-Chamber Pacing Systems and Other Imd Systems, filed Feb. 2, 2017.

U.S. Appl. No. 16/819,690, filed Mar. 16, 2020.

Non-final Office Action dated Mar. 24, 2021, U.S. Appl. No. 16/819,690, filed Mar. 16, 2020.

Response to Office Action dated Jun. 21, 2021, U.S. Appl. No. 16/819,690, filed Mar. 16, 2020.

Notice of Allowance dated Jul. 14, 2021, U.S. Appl. No. 16/819,690, filed Mar. 16, 2020.

* cited by examiner

MANAGING COMMUNICATION INTERFERENCE IN LEADLESS DUAL-CHAMBER PACING SYSTEMS AND OTHER IMD SYSTEMS

PRIORITY CLAIM

This application is a continuation U.S. patent application Ser. No. 16/819,690, filed Mar. 16, 2020, which issued as U.S. Pat. No. 11,097,112, which is a continuation of U.S. patent application Ser. No. 15/976,788, filed May 10, 2018, which issued as U.S. Pat. No. 10,632,315. Priority is claimed to each of the above applications, and each of the above applications is incorporated herein by reference in its entirety.

RELATED APPLICATIONS

This application is related to the following commonly assigned patent applications, each of which is incorporated herein by reference: U.S. patent application Ser. No. 15/413,820, titled MITIGATING EXCESSIVE WAKEUPS IN LEADLESS DUAL-CHAMBER PACING SYSTEMS AND OTHER IMD SYSTEMS FIELD OF TECHNOLOGY, filed Jan. 24, 2017; U.S. patent application Ser. No. 15/423,404, titled MITIGATING FALSE MESSAGING IN LEADLESS DUAL-CHAMBER PACING SYSTEMS AND OTHER IMD SYSTEMS, filed Feb. 2, 2017; and U.S. patent application Ser. No. 15/423,409, titled MITIGATING FALSE MESSAGING IN LEADLESS DUAL-CHAMBER PACING SYSTEMS AND OTHER IMD SYSTEMS, filed Feb. 2, 2017.

FIELD OF TECHNOLOGY

Embodiments described herein generally relate to methods and systems for communication between implantable medical devices, or communicating between a non-implantable device and an implantable medical device.

BACKGROUND

The longevity of an implantable medical device (IMD) that is powered by a battery is dependent upon how much power is consumed by electronics of the device. Such electronics can be used, e.g., for pacing or delivering other types of stimulation, sensing or otherwise collecting information, as well as for communicating within another implantable device or a non-implantable device. Accordingly, power may be consumed when pacing or delivering other types of stimulation, collecting information, as well as when communicating. It would be beneficial to reduce power consumption in order to increase the longevity of an IMD.

SUMMARY

Embodiments of the present technology relate to implantable medical devices (IMDs) and methods for use therewith. A method according to an embodiment of the present technology includes enabling a communication capability of an IMD during a message alert period, and monitoring for a message while the communication capability of the IMD is enabled during the message alert period. In response to receiving a message during the message alert period, there is a determination whether the message is valid or invalid. In response to determining that the message is invalid, the message is ignored and an invalid message count is incremented. Monitoring for a further message during the message alert period occurs, when the invalid message count has not yet reached a corresponding invalid message count threshold. The communication capability of the IMD is disabled for a disable period, when the invalid message count reaches the corresponding invalid message count threshold. In response to determining that a received message is valid, the IMD acts upon information included in the message.

In accordance with certain embodiments, the communication capability of the IMD, which is enabled during the message alert period, and which is disabled when the invalid message count reaches the corresponding invalid message count threshold, can be: a receiver of the IMD itself, an input to the receiver of the IMD, and/or an output from the receiver of the IMD.

In accordance with certain embodiments, the IMD includes a first receiver and a second receiver, wherein the first receiver is used to selectively wakeup the second receiver, and wherein the second receiver when awake consumes more power than the first receiver. The method can be used to reduce how often the first receiver wakes up the second receiver and thereby reduces how much power is consumed by the second receiver. In such an embodiment, the communication capability of the IMD, which is enabled during the message alert period, and which is disabled when the invalid message count reaches the corresponding invalid message count threshold, can be: the first receiver itself, an input to the first receiver, and/or an output from the first receiver.

In accordance with certain embodiments, the disable period during which the communication capability of the IMD is disabled, in response to the invalid message count reaching the corresponding invalid message count threshold, comprises a specified number of cardiac cycles, or a specified number of units of time.

In accordance with certain embodiments, the invalid message count threshold is specified in dependence on whether a valid message was detected during an immediately preceding message alert period. For example, the invalid message count threshold can be reduced if a valid message was not detected during an immediately preceding message alert period, compared to if a valid message was detected during the immediately preceding message alert period.

In accordance with certain embodiments, a length of the disable period during which the communication capability of the IMD is disabled, in response to the invalid message count reaching the corresponding invalid message count threshold, depends on which one of a plurality of operational modes the IMD is set to, and thus, operating in. Exemplary operational modes that an IMD can be set to include, but are not limited to, a normal operational mode, a magnetic resonance imaging (MRI) ready operational mode, or a radio frequency (RF) ablation ready operational mode.

In accordance with certain embodiments, the invalid message count threshold depends on which one of a plurality of operational modes the IMD is set to, and thus, operating in.

In accordance with certain embodiments, an amount by which the invalid message count is incremented, in response to determining that a message received during a message alert period is invalid, is greater if a valid message was not detected during an immediately preceding message alert period, compared to if a valid message was detected during the immediately preceding message alert period.

In accordance with certain embodiments, when the communication capability of the IMD is disabled the IMD enters a noise state during which the IMD operates in a safe pacing mode, and wherein once the IMD has entered the noise state the IMD does not exit the noise state until a valid message is received in a specified number of consecutive message alert periods.

An implantable medical device (IMD) according certain embodiments of the present technology includes a receiver configured to monitor for a message transmitted by another IMD or a non-implanted device. The IMD also includes a processor or controller configured to control or track message alert periods and configured to enable a communication capability associated with the receiver during each message alert period. The processor or controller can also be configured to perform the following in response to the receiver receiving a message during a message alert period: determine whether the message is valid or invalid; ignore the message and increment an invalid message count, in response to determining that the message is invalid; keep the communication capability associated with the receiver enabled during the message alert period, when the invalid message count has not yet reached a corresponding invalid message count threshold; and disable the communication capability associated with the receiver for a disable period, when the invalid message count reaches the corresponding invalid message count threshold. Additionally, the processor or controller can be configured to act upon information included in a received message, in response to determining that the received message is valid.

In accordance with certain embodiments, the communication capability associated with the receiver, which is enabled during the message alert period, and which is disabled when the invalid message count reaches the corresponding invalid message count threshold, comprises at least one of an input to the receiver or an output from the receiver.

In accordance with certain embodiments, the receiver that is configured to monitor for a message is a first receiver, and the IMD also includes a second receiver that is selectively awakened by the first receiver, wherein the second receiver when awake consumes more power than the first receiver. In such an embodiment, the communication capability associated with the receiver, which is enabled during the message alert period, and which is disabled when the invalid message count reaches the corresponding invalid message count threshold, can be an input to the first receiver and/or an output from the first receiver.

In accordance with certain embodiments, the disable period during which the communication capability associated with the receiver is disabled, in response to the invalid message count reaching the corresponding invalid message count threshold, comprises a specified number of cardiac cycles or a specified number of units of time.

In accordance with certain embodiments, the processor is configured to reduce the invalid message count threshold if a valid message was not detected during an immediately preceding message alert period, compared to if a valid message was detected during the immediately preceding message alert period.

In accordance with certain embodiments, the IMD is capable of operating in a plurality of operation modes, and a length of the disable period during which the communication capability associated with the receiver is disabled, in response to the invalid message count reaching the corresponding invalid message count threshold, depends on which one of the plurality of operational modes the IMD is set to, and thus, operating in.

In accordance with certain embodiments, when the communication capability associated with the receiver is disabled the IMD enters a noise state during which the IMD operates in a safe pacing mode, and wherein once the IMD has entered the noise state the IMD does not exit the noise state until a valid message is received in a specified number of consecutive message alert periods.

Methods according to certain embodiments of the present technology are for use by an IMD including a first receiver and a second receiver, wherein the first receiver is used to selectively wakeup the second receiver, and wherein the second receiver when awake consumes more power than the first receiver. Such methods can reduce how often the first receiver wakes up the second receiver and thereby reduce how much power is consumed by the second receiver. Such a method can include enabling at least one of the first receiver, an input to the first receiver, or an output from the first receiver during a message alert period, and monitoring for a message during the message alert period. Such a method can also include, in response to receiving a message using the first receiver during the message alert period, waking up the second receiver and using the second receiver to determine whether the message is valid or invalid. In response to determining that the message is invalid, the message is ignored and an invalid message count is incremented. Monitoring for a further message occurs during the message alert period, when the invalid message count has not yet reached a corresponding invalid message count threshold. At least one of the first receiver, an input to the first receiver, or an output from the first receiver is disable for a disable period, when the invalid message count reaches the corresponding invalid message count threshold. In response to a valid message being received, information included in the message is acted upon.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

In some embodiments of an illustrative cardiac pacing system, pacing and sensing operations of multiple medical devices, which may include one or more leadless cardiac pacemakers, an implantable cardioverter-defibrillator (ICD), such as a subcutaneous-ICD, and/or a programmer reliably and safely coordinate pacing and/or sensing operations.

Figure 1:
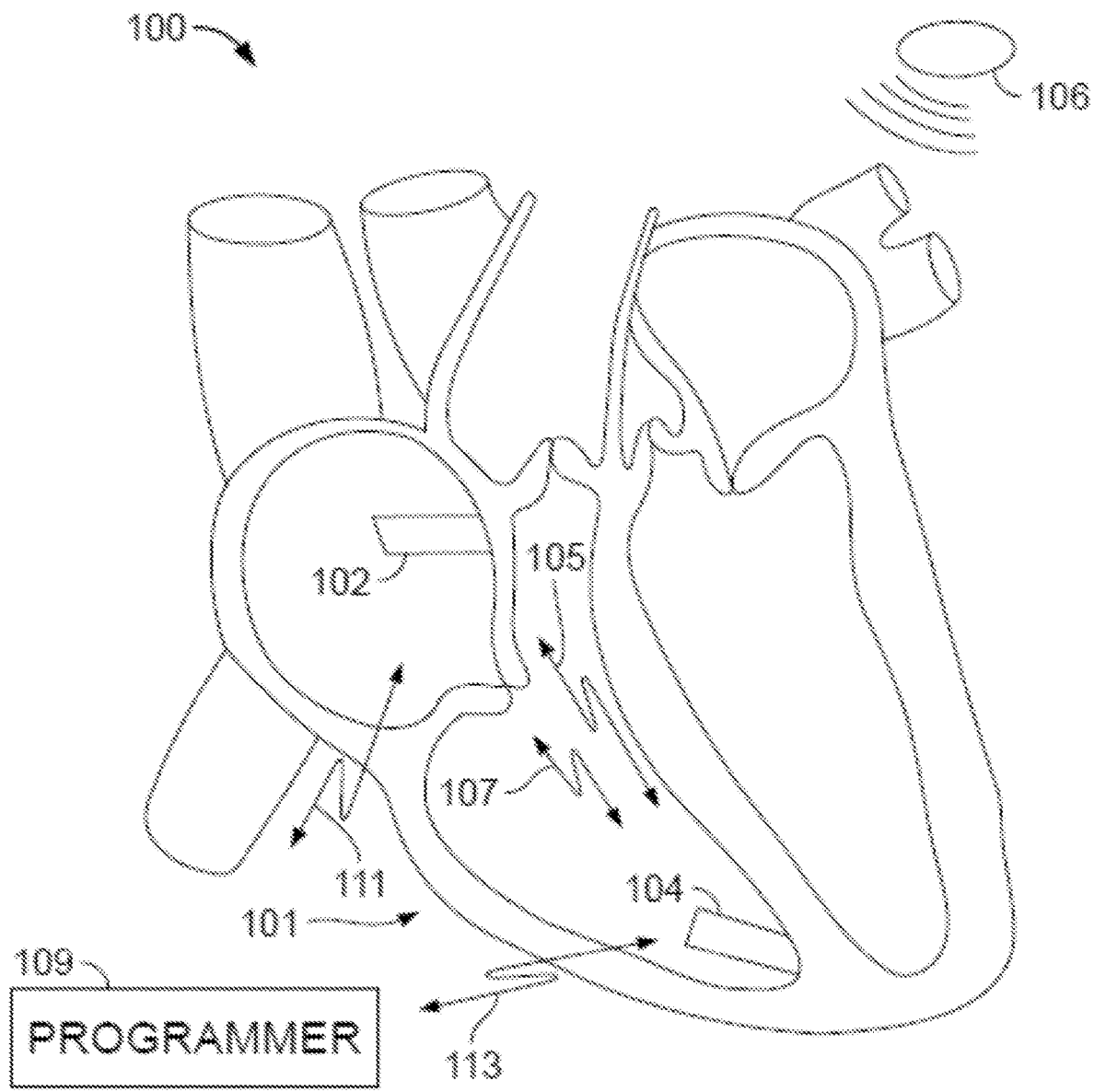
FIG. 1 illustrates a system formed in accordance with certain embodiments herein as implanted in a heart.

FIG. 1 illustrates a system 100 formed in accordance with certain embodiments herein as implanted in a heart 101. The system 100 comprises two or more leadless pacemakers (LPs) 102 and 104 located in different chambers of the heart. LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In some embodiments, LPs 102 and 104 communicate with one another, with an ICD 106, and with an external device (programmer) 109 through wireless transceivers, communication coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more leadless cardiac pacemakers 102 and 104 can be co-implanted with the implantable cardioverter-defibrillator (ICD) 106. Each leadless cardiac pacemaker 102, 104 uses two or more electrodes located within, on, or within a few centimeters of the housing of the pacemaker, for pacing and sensing at the cardiac chamber, for bidirectional communication with one another, with the programmer 109, and the ICD 106.

In accordance with certain embodiments, methods are provided for coordinating operation between leadless pacemakers (LPs) located in different chambers of the heart. The methods configure a local LP to receive communications from a remote LP through conductive communication.

While the methods and systems described herein include examples primarily in the context of LPs, it is understood that the methods and systems herein may be utilized with various other external and implanted devices. By way of example, the methods and systems may coordinate operation between various implantable medical devices (IMDs) implanted in a human, not just LPs. The methods and systems comprise configuring a first IMD to receive communications from at least a second IMD through conductive communication over at least a first channel. It should also be understood that the methods and systems may coordinate operation between multiple IMDs, and are not limited to coordinate operation between just a first and second IMD. The methods and systems may also be used to coordinate operation of two or more IMDs implanted within the same chamber that may be the same type of IMD or may be different types of IMDs. The methods and systems may also be used to coordinate operation of two or more IMDs in a system comprising at least one IMD implanted but not within a heart chamber, e.g., epicardially, transmurally, intravascularly (e.g., coronary sinus), subcutaneously (e.g., S-ICD), etc.

Figure 2:
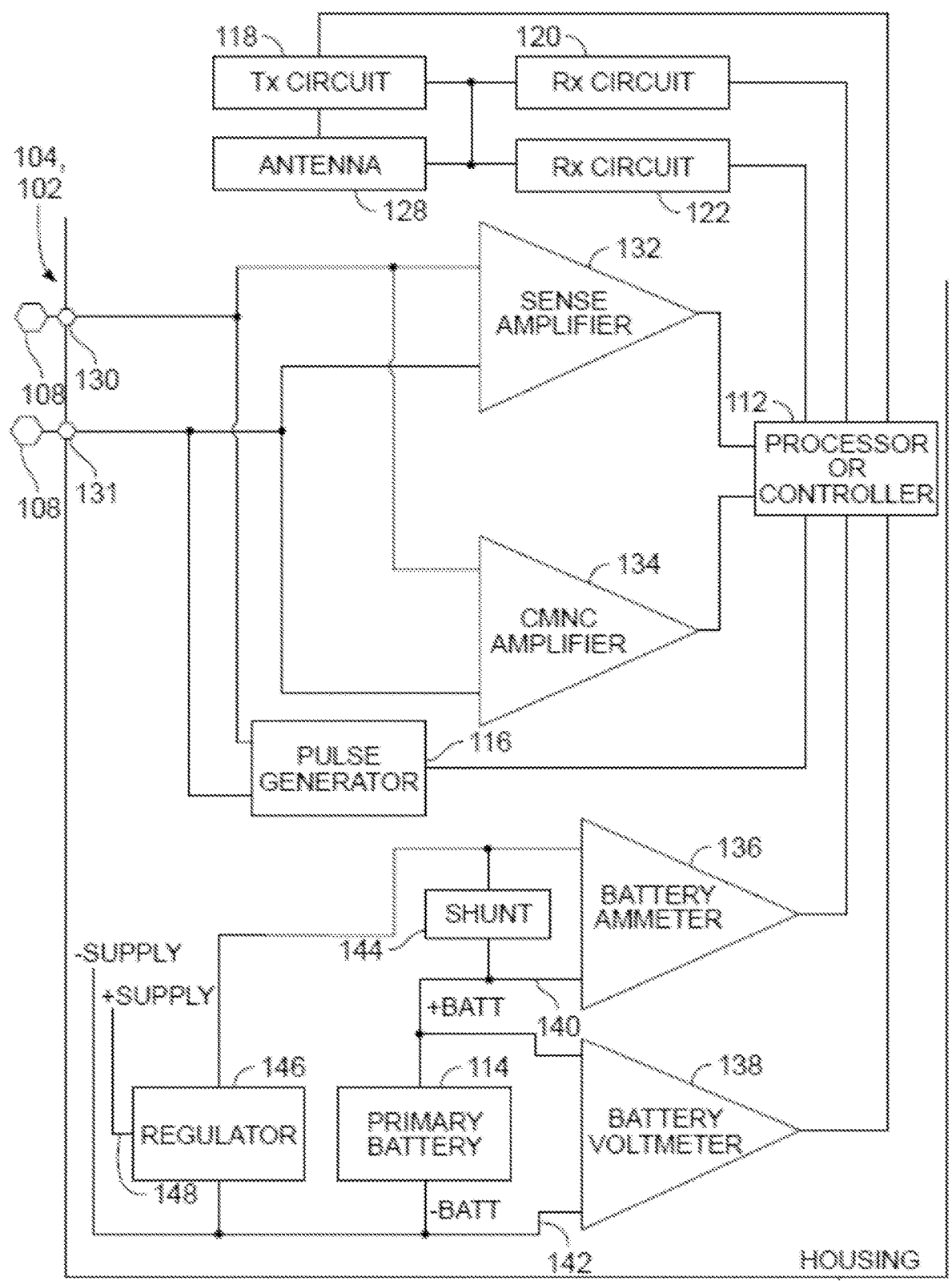
FIG. 2 is a block diagram of a single leadless pacemaker (LP) in accordance with certain embodiments herein.

Referring to FIG. 2, a pictorial diagram shows an embodiment for portions of the electronics within LP 102, 104 configured to provide conducted communication through the sensing/pacing electrode. One or more of LPs 102 and 104 comprise at least two leadless electrodes 108 configured for delivering cardiac pacing pulses, sensing evoked and/or natural cardiac electrical signals, and uni-directional or bi-directional communication.

LP 102, 104 includes a transmitter 118 and first and second receivers 120 and 122 that collectively define separate first and second communication channels 105 and 107 (FIG. 1), (among other things) between LPs 102 and 104. Although first and second receivers 120 and 122 are depicted, in other embodiments, LP 102, 104 may only include first receiver 120, or may include additional receivers other than first and second receivers 120 and 122. LP 102, 104 may also include one or more transmitters in addition to transmitter 118. In certain embodiments, LPs 102 and 104 may communicate over more than just first and second communication channels 105 and 107. In certain embodiments, LPs 102 and 104 may communicate over one common communication channel 105. The transmitter 118 and receiver(s) 120, 122 may each utilize a separate antenna or may utilize a common antenna 128. Optionally, LPs 102 and 104 communicate conductively over a common physical channel via the same electrodes 108 that are also used to deliver pacing pulses. Usage of the electrodes 108 for communication enables the one or more leadless cardiac pacemakers 102 and 104 for antenna-less and telemetry coil-less communication.

When LP 102, 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice or wakeup pulse) followed by an event marker. The notice trigger pulse is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any implant to implant (i2i) communication from another LP (or other IMD) or from an external device may transmit a receive acknowledgement indicating that the receiving LP/IMD received the i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Some embodiments described herein provide efficient and reliable processes to maintain synchronization between LPs 102 and 104 without maintaining continuous communication between LPs 102 and 104. In accordance with certain embodiments herein, the transmitter(s) 118 and receiver(s) 120, 122 utilize low power event messages/signaling between multiple LPs 102 and 104. The low power event messages/signaling may be maintained between LPs 102 and 104 synchronously or asynchronously.

For synchronous event signaling, LPs 102 and 104 maintain synchronization and regularly communicate at a specific interval. Synchronous event signaling allows the transmitter and receivers in each LP 102,104 to use limited (or minimal) power as each LP 102, 104 is only powered for a small fraction of the time in connection with transmission and reception. For example, LP 102, 104 may transmit/receive (Tx/Rx) communications in time slots having duration of 10-20 μs, where the Tx/Rx time slots occur periodically (e.g., every 10-20 ms). In the foregoing example, a receiver 120, 122 that is active/ON (also referred to as awake) for select receive time slots, that are spaced apart several milliseconds, may draw an amount of current that is several times less (e.g., 1000× less) than a current draw of a receiver that is "always on" (always awake).

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. During asynchronous event signaling, one or more of receivers 120 and 122 of LPs 102 and 104 may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of 1/500 to 1/10000. A gain factor may be 1/1000th. Transmit current is a design factor in addition to receiver current. As an example, the system may allocate one-half of the implant communication current budget to the transmitter (e.g., 0.5 μA for each transmitter). When LP 102, 104 maintains a transmitter in a continuous on-state and the electrode load is 500 ohms, a transmitted voltage may be 0.250 mV. When an event signal is transmitted at 0.250 mV, the event signal is attenuated as it propagates and would appear at LP 102, 104 receiver as an amplitude of approximately 0.25 μV. The receivers 120 and 122 utilize a synchronization threshold to differentiate incoming communication signals from noise. As an example, the synchronization threshold may be 0.5 μV (or more generally 0.25 μV to 5 μV), which would cause LP 102, 104 receiver to reject an incoming communication signal that exhibits a receive voltage below 0.5 μV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

When LP transmitter 118 transmits event signals over a conductive communication channel that has an electrode load of 500 ohm using a 1 ms pulse width at 2.5V at a rate of 60 bpm, LP transmitter 118 will draw 4.4 μA for transmit current. When LP transmitter 118 transmits event signals at 2.5V using a 2 μs pulse width, transmitter 118 only draws 10 nA to transmit event messages at a rate of 60 bpm. In order to sense an event message (transmitted with the foregoing parameters), receivers 120 and 122 may utilize 50 μA. In accordance with certain embodiments herein, the pulse widths and other transmit/receive parameters may be adjusted to achieve a desired total (summed) current demand from both transmitter 118 and receivers 120 and 122. The transmitter current decreases nearly linearly with narrowing bandwidth (pulse width), while a relation between receiver current and bandwidth is non-linear.

In accordance with certain embodiments herein, LPs 102 and 104 may utilize multi-stage receivers that implement a staged receiver wakeup scheme in order to improve reliability yet remain power efficient. Each of LPs 102 and 104 may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 μs to approximately 1 ms) as compared to the fundamental frequency range (e.g., greater than 100 kHz/less than 10 μs per pulse) assigned to the second receive channel. First receiver 120 may maintain the first channel active (awake) for at least a portion of a time when the second channel is inactive (asleep) to listen for event messages from a remote LP. The controller or processor determines whether the incoming signal received over the first channel corresponds to an LP wakeup notice. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP).

The marker message may represent a signature indicative of an event qualification to qualify a valid event marker pulse. The event qualification messages distinguish a message from spurious noise and avoid mistaking other signals as event messages having implant markers. The event message may be repeated to allow the LP receiver 120 multiple chances to "catch" the event qualification. Additionally or alternatively, the Tx and Rx LP 102, 104 may implement a handshaking protocol in which the Tx and Rx LP 102, 104 exchange additional information, such as to allow a response to follow the marker. The exchange of additional information may be limited or avoided in certain instances as the exchange draws additional power when sending and receiving the information. Optionally, the event message may be configured with additional content to provide a more robust event marker.

Transmitter 118 may be configured to transmit the event messages in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, programmer 109 may communicate over a programmer-to-LP channel, with LP 102, 104 utilizing the same communication scheme. The external programmer may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse width. The foregoing pacing parameters correspond to a current draw of about 1.9 µA. The same LP 102, 104 may implement an event message utilizing event signaling parameters for amplitude, pulse width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102, 104 senses an intrinsic event, the transmitter sends a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, LP 102, 104 may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102, 104 increases an extent to which LP 102, 104 uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102, 104 may use larger pulse widths.

By combining event messages and low power pacing, LP 102, 104 may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

In an embodiment, a communication capacitor is provided in LP 102, 104. The communication capacitor may be used to transmit event signals having higher voltage for the event message pulses to improve communication, such as when the LPs 102 and 104 experience difficulty sensing event messages. The high voltage event signaling may be used for implants with high signal attenuation or in the case of a retry for an ARQ (automatic repeat request) handshaking scheme.

For example, when an LP 102, 104 does not receive an event message within a select time out interval, LP 102, 104 may resend an event message at a higher amplitude. As another example, LP 102, 104 may perform an event signaling auto-level search wherein the LPs send event messages at progressively higher amplitude until receiving confirmation that an event message was received (or receiving a subsequent event message from another LP). For example, in DDD mode when the atrial or ventricular LP 102, 104 does not see an event signal from LP 102, 104 in the other chamber before its timeout interval it could automatically raise the amplitude of the event message, until the LPs 102 and 104 become and remain in sync. Optionally, LP 102, 104 may implement a search hysteresis algorithm similar to those used for rate and amplitude capture to allow the lowest safe detectible amplitude to be determined.

The LPs 102 and 104 may be programmable such as to afford flexibility in adjusting the event marker pulse width. In some embodiments, different receiver circuits may be provided and selected for certain pulse widths, where multiple receivers may be provided on a common ASIC, thereby allowing the user to vary the parameters in an LP after implant.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to leadless cardiac pacemaker 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102, 104 configured for implantation in electrical contact with a cardiac chamber and configured to perform cardiac pacing functions in combination with the co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
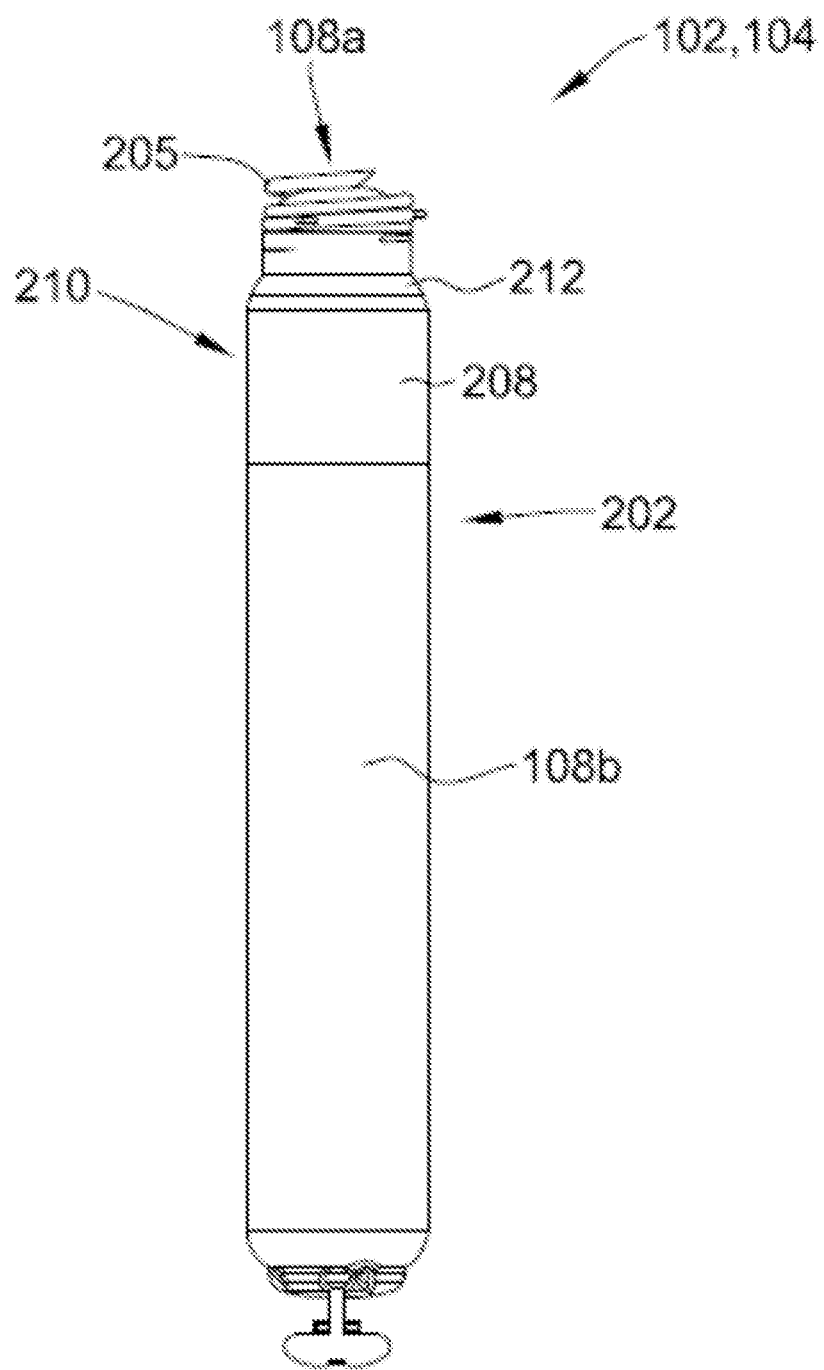
FIG. 3 illustrates a LP in accordance with certain embodiments herein.

FIG. 3 shows an LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulability tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
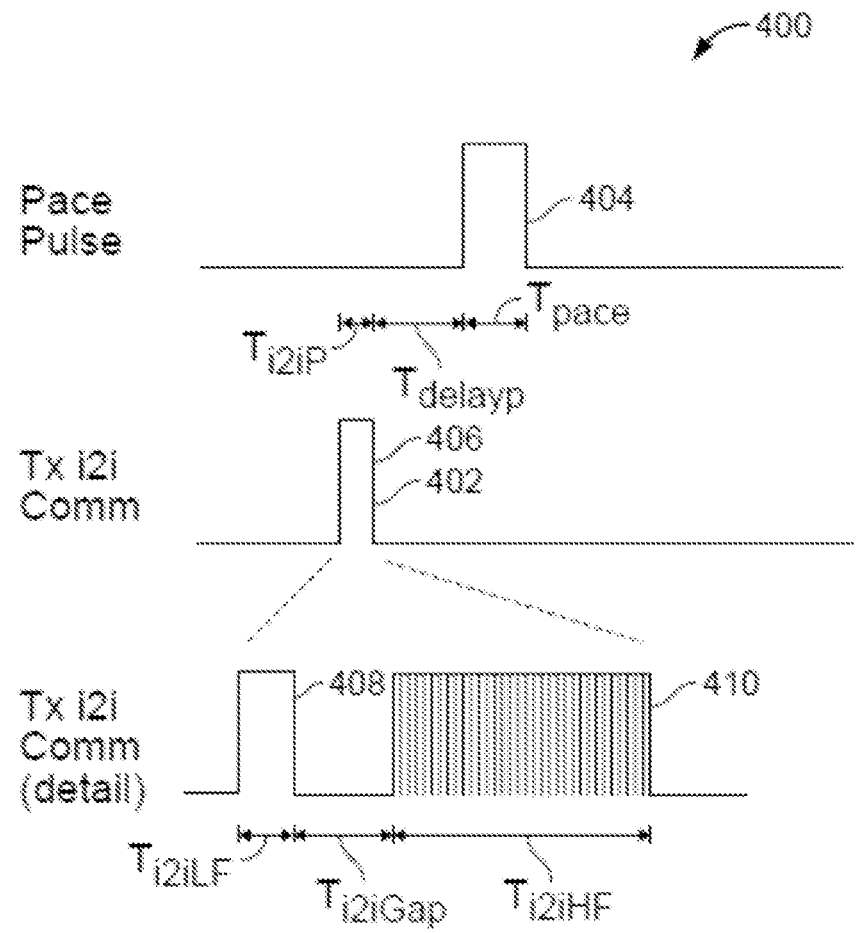
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102 to LP 104. As shown in FIG. 4, in this embodiment, an i2i transmission 402 is sent prior to delivery of a pace pulse 404 by the transmitting LP (e.g., LP 102). This enables the receiving LP (e.g., LP 104) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 5:
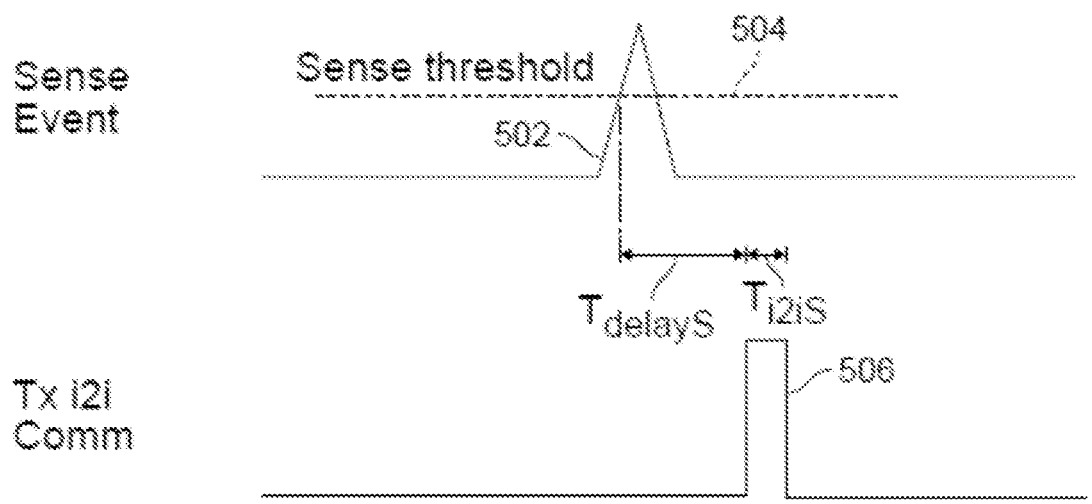
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102 to LP 104. As shown in FIG. 5, in this embodiment, the transmitting LP (e.g., LP 102) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
| --- | --- | --- |
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
| --- | --- | --- |
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a WI mode as the vLP does not depend on i2i communication to perform ventricular pace/sense activities. Once i2i communication is restored, the system 100 can automatically resume dual-chamber functionalities.

Mitigating Excessive Wakeups in Dual Chamber Leadless Pacemaker

As explained above, each of LPs 102 and 104 may include first and second receivers 120 and 122 that operate with different first and second activation protocols and different first and second receive channels. As also explained above, the first and second receivers 120 and 122 of each of the LPs 102 and 104 can enable the LPs 102 and 104 to implement a staged receiver wakeup scheme in order to improve reliability yet remain power efficient. For example, the first receiver 120 may be assigned a first activation protocol that by default causes the first receiver 120 to be normally "on" or "awake" or "active" (which terms are used interchangeably herein) and listening for messages received over a first receive channel that has a lower fundamental frequency range/pulse duration (e.g., 1 kHz to 100 kHz/10 μs to approximately 1 ms) as compared to a fundamental frequency range (e.g., greater than 100 kHz/less than 10 μs per pulse) assigned to the second receive channel. The first receiver 120 may maintain the first channel active for at least a portion of a time when the second channel is inactive, so that the first receiver 120 can listen for event messages from a remote LP. The controller or processor of the LP can determine whether the incoming signal received over the first channel corresponds to an LP wakeup notice. The second receiver 122 may be assigned a second activation protocol that is a triggered protocol, in which the second receiver 122 is normally "off" or "asleep" or "inactive" (which terms are used interchangeably herein) and becomes active in response to detection of trigger events over the first receive channel (e.g., when the incoming signal corresponds to the LP wakeup notice, activating the second channel at the local LP). In other words, in order to conserve power the second receiver 122 can be asleep unless awaken by the first receiver 120. Depending upon implementation, when the second receiver 122 is asleep, it can either be in a low power mode or completely disconnected from a power supply. Regardless of the implementation, the second receiver 122 will consume less power when it is asleep compared to when it is awake. Similarly, the first receiver 120 will consume less power when it is asleep compared to when it is awake. When both the first and second receivers are awake the second receiver consumes more power than the first receiver.

The first receiver 120 of a given LP (e.g., 102) can also be referred to as a low power low bandwidth receiver, since it is configured to operate at a lower power and a lower bandwidth than the second receiver 122 does when the second receiver 122 is awake. Conversely, the second receiver 122 of the LP (e.g., 102) can also be referred to as a high power high bandwidth receiver, since it is configured to operate at a higher power and a higher bandwidth than the first receiver 120 does when the second receiver 122 is awake. In accordance with certain embodiments of the present technology, in order to conserve power, as part of i2i communication, a signal received by the low power low bandwidth receiver (i.e., the first receiver 120) is used to wakeup the high power high bandwidth receiver (i.e., the second receiver 122), using what can be referred to as a two-step wakeup process. In the two-step wakeup process, the first receiver 120 of a device (e.g., the LP 102) can be normally awake and listening for messages while the second receiver 122 is normally asleep and only woken up by the first receiver 120 when the first receiver 120 receives a portion of a message (e.g., the low frequency pulse 408) that also includes another portion (e.g., the high frequency pulse train 416) that is to be received and decoded using the second receiver 122.

A potential problem with the aforementioned two-step wakeup process is that the low power low bandwidth receiver (i.e., the first receiver 120) may be very sensitive to electrical noise, such as, but not limited to, electromagnetic interference (EMI). More specifically, in an electrically noisy environment, the high sensitivity of the first receiver 120 to electrical noise may cause the first receiver 120 to frequently trigger wakeups of the second receiver 122 when unnecessary. This can lead to significant power consumption and a shorter battery life of the LP, and thus, a reduction in the useful life of the LP (e.g., 102). A triggered wakeup of the second receiver 122 is considered unnecessary, for example, where the wakeup was triggered in response to noise that was mistaken for a valid message, as opposed to being triggered in response to an actual valid message being received from another LP (e.g., 104). Exemplary types of valid messages that an LP (e.g., 102) can receive from another LP (e.g., 104) include, but are not limited to, the event messages that were described above with reference to FIGS. 1-5 and Tables 1 and 2.

Certain embodiments of the present technology, which are described below, mitigate and preferably prevent the first receiver 120 from unnecessarily waking up the second receiver 122 of a device, such as an LP (e.g., 102). Such embodiments are beneficial because they can reduce power consumption and increase battery life of the LP, and thus, increase the useful life of the LP (e.g., 102).

Even with various layers of data integrity protection, there is still the relatively low possibility that noise may be detected as a valid message, resulting in a false positive. For example, noise that is received and is mistaken for being an actual message and is decoded by the IMD because the noise is sufficiently similar to an actual message is an example of how a false positive can occur. In accordance with certain embodiments of the present technology, monitoring for messages is temporarily suspended when it is determined that an unacceptable amount of noise is present, thereby reducing the probability that a false positive detection of a message occurs.

In certain embodiments, if the first receiver 120 triggers the wakeup of the second receiver 122, but the triggered wakeup is not followed (within a specified amount of time) by the second receiver 122 receiving and decoding a valid message, then the wakeup is considered invalid, or more generally, the received message that caused the first receiver 120 to wakeup the second receiver 122 can be considered an invalid message.

In accordance with certain embodiments, a device (e.g., the LP 102) temporarily disables at least one of its communication capabilities when an amount of invalid messages received during a message alert period reaches (e.g., equals or exceeds) a specified threshold. The period during which the device temporarily disables at least one of its communication capabilities is often referred to herein as a disable period. In accordance with certain embodiments, during the disable period the device enters a Noise State. While in the Noise State, which can also be referred to as a noise reversion state, or a communication noise reversion state, the device can operate in a safe pacing mode (e.g., VVI or VOO) that does not depend on i2i communication. After the disable period expires, i.e., has ended, the device can return to attempting to detect a valid message during a next message alert period, and may trigger another disable period if again an amount of invalid messages received during the message alert period reaches a specified threshold (which can be the same threshold, or a different threshold than used in the preceding message alert period).

In certain embodiments, the device can exit the Noise State whenever the disable period expires. Alternatively, and preferably, once the device enters the Noise State, the device remains in the Noise State (during which time the device operates in a safe pacing mode) until one valid message is (or some other specified number of valid messages are) received, at which point the device exits the Noise State and returns to its normal pacing mode.

The above summarized embodiments can be used to mitigate and preferably prevent a first receiver (e.g., 120) from unnecessarily waking up a second receiver (e.g., 122) of a device, such as an LP (e.g., 102). Such embodiments can also be used to reduce the chance of an invalid message being mistaken for being a valid message. In other words, such embodiments can be used to reduce false positive detections of valid messages. By temporarily disabling a communication capability (e.g., the first receiver 120 itself, its input and/or its output) of a device (e.g., LP 102), and/or reducing how often a first receiver (e.g., 120) unnecessarily wakes up a second receiver (e.g., 122) of a device, such as an LP (e.g., 102), embodiments of the present technology can be used to conserve power and thus improve battery and device longevity. Certain such embodiments of the present technology are described below with reference to the high level flow diagram of FIG. 6A. The methods described with reference to FIG. 6A, and with reference to FIG. 6B, can be performed under the control of a processor or controller (e.g., 112 in FIG. 2, or 720 in FIG. 7). In other words, a processor or controller can be configured to perform various aspects of the present technology.

Figure 6A:
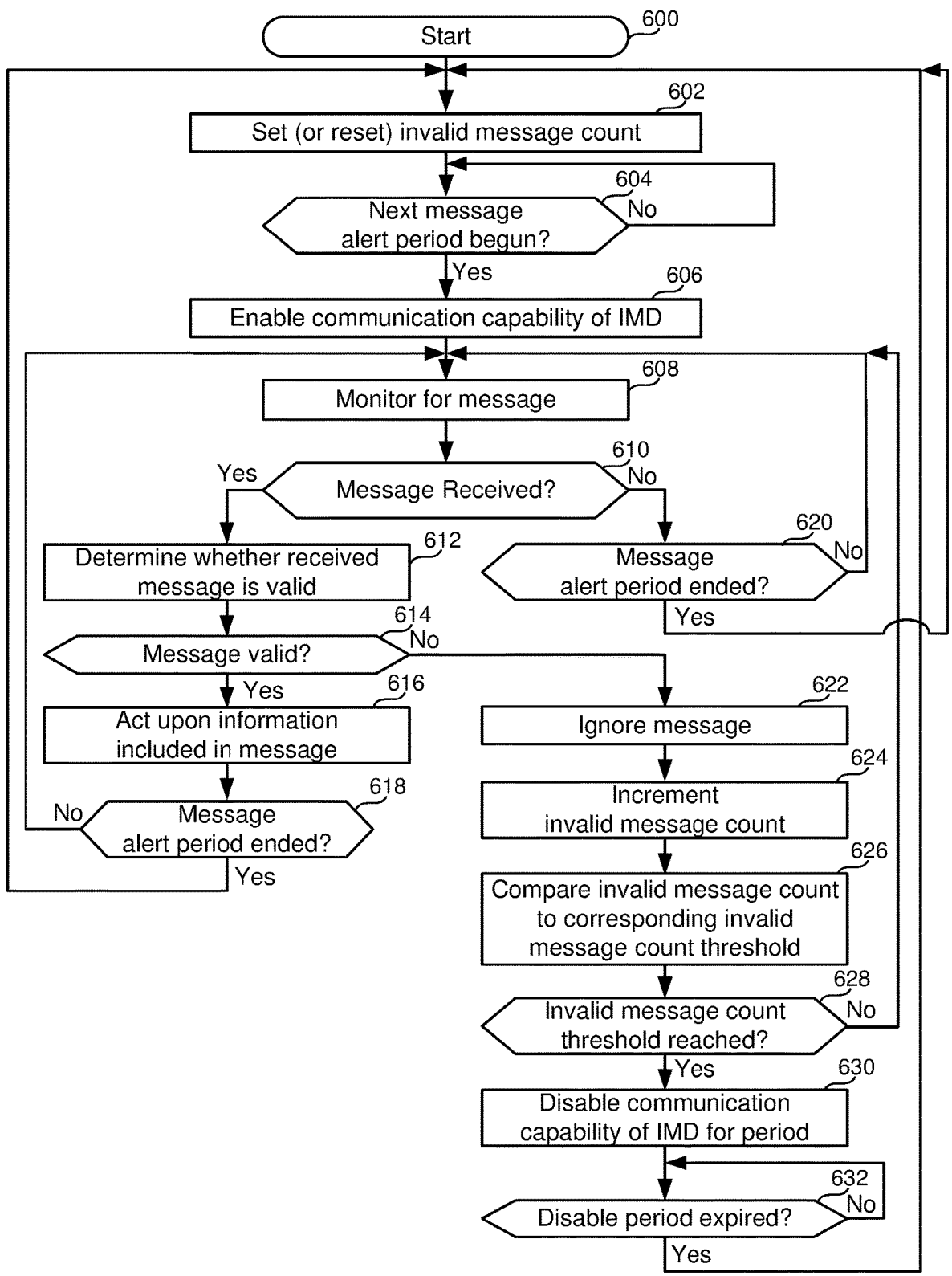
FIGS. 6A and 6B are high level flow diagrams that are used to summarize methods according to various embodiments of the present technology that are for use by an IMD, such as an LP, and which methods can be used, for example, to reduce how often a first receiver of a device wakes up a second receiver of the device and thereby reduces power consumed by the device, but are not limited thereto.

Referring to FIG. 6A, block 600, labeled "Start", is the entry point for the method. At a step 602, an invalid message count is set, or reset, to its initial value, which can be zero, but is not limited thereto. At step 604 there is a determination of whether a next message alert period has begun, wherein the message alert period is a period during which an IMD that is performing the method monitors for a message (i.e., listens for a message). In certain embodiments, a message alert period is related to a cardiac cycle, and may occur during an entire cardiac cycle, or just a portion of a cardiac cycle. For example, where an IMD performing the method is implanted in a ventricle, a message alert period can be a portion of a cardiac cycle that follows an AV delay, a blanking period and/or a relative refractory period, but is not limited thereto. In such an embodiment, if the decision at step 604 occurs, e.g., during an AV delay or a blanking period, then the answer to the decision at step 604 would be No, and step 604 would be repeated in a loop until the answer to the decision at step 604 is Yes, at which point flow would go to step 606. For another example, where an IMD performing the method is implanted in an atrium, a message alert period can be a portion of a cardiac cycle that follows a post ventricular atrial blanking (PVAB) period, a post ventricular atrial refractory period (PVARP) and/or some other alternatively-defined atrial refractory period. In such an embodiment, if the decision at step 604 occurs, e.g., during an atrial blanking or refractory period, then the answer to the decision at step 604 would be No, and step 604 would be repeated in a loop until the answer to the decision at step 604 is Yes, at which point flow would go to step 606.

At step 606, a communication capability of the IMD is enabled. Referring briefly back to FIG. 2, in accordance with certain embodiments, the communication capability that is enabled at step 606 can relate to the first receiver 120 of the IMD, and more specifically, can be the receiver 120 itself, an input to the first receiver 120, or an output from the first receiver 120.

At step 608, a message is monitored for (e.g., listened for) by the IMD, and more specifically, by a receiver (e.g., the first receiver 120) of the IMD (e.g., an LP 102 or 104).

At step 610 there is a determination of whether a message was received. If the answer to the determination at step 610 is No (i.e., if a message was not received), then at step 620 there is a determination of whether the message alert period has ended. If the answer to the determination at step 620 is No (i.e., if the message alert period has not ended), then flow returns to step 608. If the answer to the determination at step 620 is Yes (i.e., if the message alert period has ended), then flow returns to step 602. In accordance with certain embodiments, in order to conserver power, and thus a battery and/or device life, during the period of time between when a message alert period has ended and when a next message alert period begins, a receiver and/or transmitter (and or/one or more other components of an IMD) can be disabled or put into a low power mode.

If the answer to the determination at step 610 is Yes (i.e., if a message was received), then at step 612 there is a determination of whether the received message is valid. The term "message", as used herein, can refer to an actual sent message that is received and is capable of being decoded by the second receiver 122, an actual sent message that is received but is too noisy to be decoded by the second receiver 122, an actual sent message that is received but due to noise it is decoded mistakenly for a different message, noise that is initially mistaken for being an actual message but is sufficiently different than an actual message so that it cannot be decoded by the second receiver 122, as well as noise that is received and is mistaken for being an actual message and is decoded by the IMD because the noise is sufficiently similar to an actual message. The term "valid message", as used herein, can refer to an actual sent message that is received and is capable of being decoded by the second receiver 122, an actual sent message that is received but due to noise it is decoded mistakenly for a different message (this may occur in rare circumstances), or noise that is received and is mistaken for being an actual message and is decoded by the IMD because the noise is sufficiently similar to an actual message (this may occur in very rare circumstances). The latter two types of a "valid message", which may occur in rare or very rare circumstances, are examples false positives. Accordingly, it is possible that a "valid message" is not an actual message, or is an actual message that has been decoded incorrectly. The term "invalid message", as used herein, can refer to an actual sent message that is received but is too noisy to be decoded by the second receiver 122, as well as noise that is initially mistaken for being an actual message but is sufficiently different than an actual message so that it cannot be decoded by the second receiver 122. In accordance with certain embodiments, the determination of whether a message is valid or invalid can be performed by a processor or controller that performs decoding and error detection or correction.

At step 614 there is a determination of whether the received message was determined to be valid at step 612. While steps 614 and 612 are shown as separate steps in FIG. 6A, these two steps could have instead been shown as a single step. For example, the block labeled 620 in FIG. 6A can be removed and the "No" path from block 610 can instead go to block 618. For another example, the block labeled 618 in FIG. 6A can be removed and flow can go directly from block 616 to block 620.

Still referring to FIG. 6A, if the answer to the determination at step 614 is No (i.e., if a valid message was not received), then flow goes to step 622, and the received message (which was determined to have been not valid, or invalid) is ignored. At step 624 the invalid message count is incremented. For example, the equation imc=imc+1 can be used at step 624, where imc is the invalid message count, which is set or reset each time step 602 is performed. At step 626 the invalid message count is compared to an invalid massage count threshold (imct), and at step 628 that is a determination of whether the invalid message count threshold (imct) has been reached. If the answer to the determination at step 628 is No (i.e., if the invalid message count threshold has not been reached), then flow returns to step 608 and monitoring for another message occurs. If the answer to the determination at step 628 is Yes (i.e., if the invalid message count threshold has been reached), that is indicative of electromagnetic interference (EMI) and/or other noise being present, and thus, at step 630 the communication capability (that was enabled at step 606) is disabled for a disable period. While steps 626 and 628 are shown as two separate steps, those steps can alternatively be combined into a single step.

The disable period, which is a period during which a communication capability of the device performing the method is disabled, can be specified in units of time, e.g., a specified number of seconds. For example, the disable period can be 2 seconds, 4 seconds, or 10 seconds, but is not limited thereto. Alternatively, the disable period can be specified as a number (N) of cardiac cycles, or other types of cycles, where N is an integer that is equal to or greater than 1. For example, the disable period can be 2 cardiac cycles, 4 cardiac cycles, or 10 cardiac cycles, but is not limited thereto. Where the method being described is performed independently by an LP 102 implanted in an atrium, as well as by an LP 104 implanted in a ventricle, what the LP 102 considers a cardiac cycle may differ from what the LP 104 considers a cardiac cycle, because the LPs 102 and 104 have different frames of reference. For example, the LP 102 may consider a cardiac cycle as the period between two atrial (paced or sensed) events, whereas the LP 104 may consider a cardiac cycle as the period between two ventricular (paced or sensed) events.

After the communication capability is disabled at step 630, then flow goes to step 632 where there is a determination of whether the disable period has expired. Until the disable period expires, step 632 is repeated in a loop until the answer to the decision at step 632 is Yes, at which point flow would return to step 602, as shown in FIG. 6A.

At step 630, the communication capability of the IMD that is disabled can be a communication capability related to a receiver and/or a transmitter of the IMD. For example, referring briefly back to FIG. 2, in accordance with certain embodiments, the communication capability that is disabled at step 630 can relate to the first receiver 120 of the IMD, and more specifically, can be the first receiver 120 itself, an input to the first receiver 120, and/or an output from the first receiver 120. For example, disabling the communication capability related to the first receiver 120 of the IMD, at step 630, can involve disconnecting the input to the first receiver 120, forcing the output of the first receiver 120 inactive, and/or ignoring the output of the first receiver 120. In other words, at step 630 the first receiver 120 itself can be disabled, the input to the first receiver 120 can be disabled by disconnecting the input, and/or an output from the first receiver 120 can be disabled by forcing the output of the first receiver 120 inactive and/or ignoring the output of the first receiver 120. Other variations are also possible and within the scope of the embodiments described herein. Additionally, in accordance with certain embodiments, a communication capability related to the transmitter of the IMD (e.g., 118 in FIG. 2) can be disabled during the disable period, which in one embodiment may be achieved by not activating the transmitter during the disable period.

Returning to the discussion of step 614 in FIG. 6A, if the answer to the determination at step 614 is Yes (i.e., if a valid message was received), then flow goes to step 616, and information included in the valid message is acted upon. Where the IMD (e.g., LP 104) performing the method is implanted in a ventricle, the information included in the valid message (e.g., received from another IMD, e.g., LP 102, implanted in an atrium) can be an atrial sense (AS) notification of a sensed event in atrium that causes the IMD to initiate an AV interval, or an atrial pace (AP) notification of a paced event in atrium that causes the IMD to initiate a post ventricular atrial blanking (PVAB) interval, some other alternatively-defined atrial blanking period, or an AV interval (if not in PVARP). Where the IMD (e.g., LP 102) performing the method is implanted in an atrium, the information included in the valid message (e.g., received from another IMD, e.g., LP 104, implanted in a ventricle) can be a ventricular sense (VS) notification of a sensed event in a ventricle that causes the IMD to initiate a PVARP interval, or an ventricular pace (VP) notification of a paced event in ventricle that causes the IMD to initiate a PVAB interval or a PVARP interval, or an atrial pace (AP) command that causes the IMD to immediately deliver a pace pulse in the atrium. These are just a few examples, which are not intended to be all encompassing.

Still referring to FIG. 6A, after (or while) step 616 is being performed, at step 618 there is a determination of whether the message alert period has ended. If the answer to the determination at step 620 is No (i.e., if the message alert period has not ended), then flow returns to step 608. If the answer to the determination at step 620 is Yes (i.e., if the message alert period has ended), then flow returns to step 602. As can be appreciated from FIG. 6A, step 618 and 620 are the same, and thus, the flow diagram in FIG. 6A can be redrawn to include just one of those steps, as was explained above when discussing step 618. In certain embodiments it is possible that more than one valid message can be received during a same message alert period. For example, if an LP (e.g., 104) implanted within a ventricle detects an R wave and soon thereafter detects a premature ventricular contraction (PVC), this may result in another LP (e.g., 102) implanted within an atrium receiving more than one valid message within a same message alert period.

The invalid message count threshold (imct), referred to at steps 626 and 628, can be a value that is either set by default or by a physician or clinician, which once set, is not changed on the fly by the IMD that is performing the method summarized with reference to FIG. 6A. In alternative embodiments, described below with reference to FIG. 6B, the IMD can change the invalid message count threshold (imct) on the fly, in dependence on whether a valid message was detected during an immediately preceding message alert period. More specifically, the invalid message count threshold (imct) can be reduced if a valid message was not detected during an immediately preceding message alert period, compared to if a valid message was detected during the immediately preceding message alert period. Accordingly, this method variant effectively makes it more difficult for the IMD to exit from a Noise State that the IMD enters during the disable period, assuming the IMD is configured to remain in the Noise State (once the Noise State is entered) until a valid message (or a specified number of valid messages) are thereafter received. Alternatively, the invalid message count threshold (imct) can be increased if a valid message was not detected during an immediately preceding message alert period, compared to if a valid message was detected during the immediately preceding message alert period. More generally, in certain embodiments the invalid message count threshold can be specified in dependence on whether a valid message was detected during an immediately preceding message alert period.

Figure 6B:
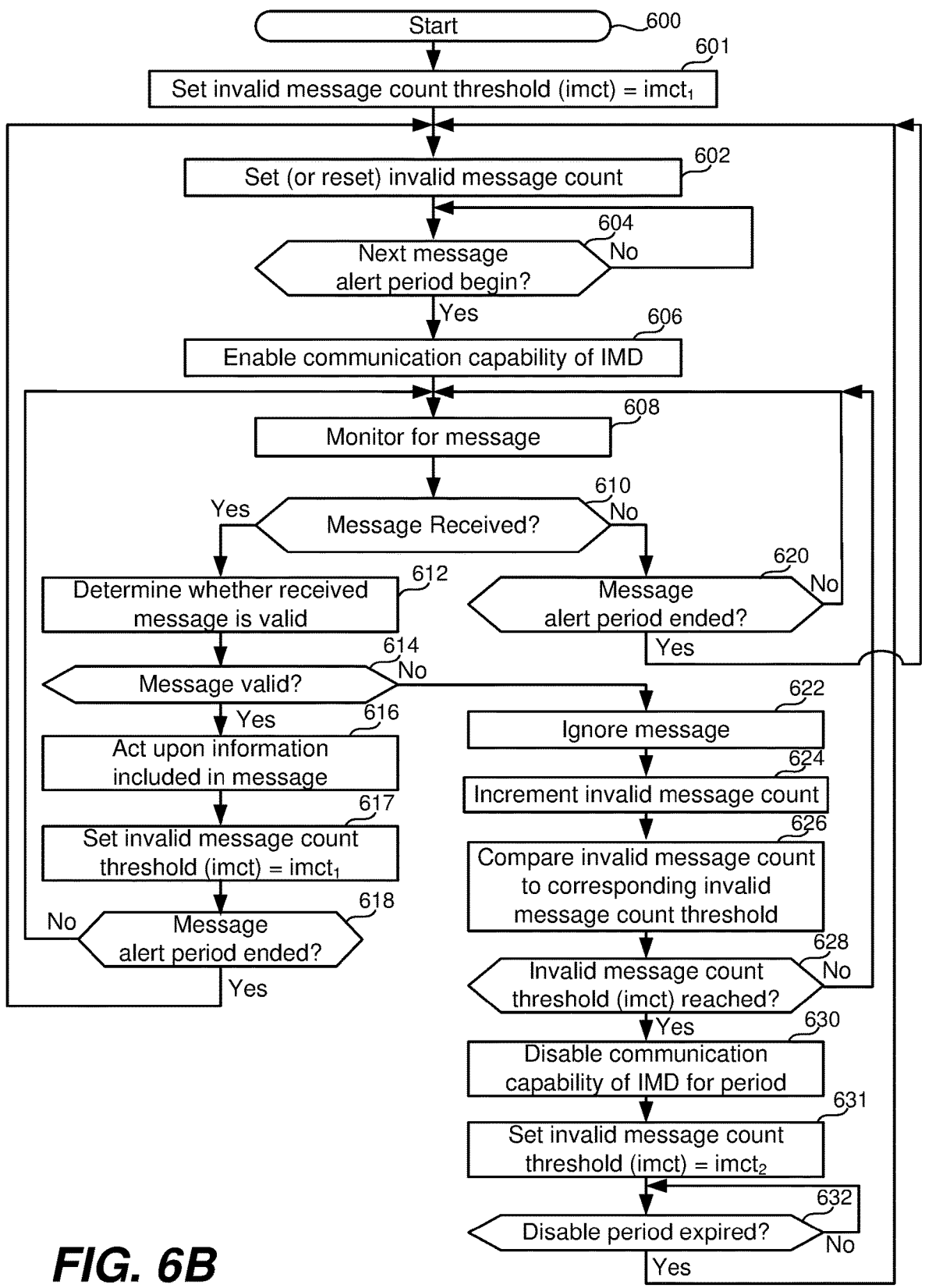

Referring to FIG. 6B, most of the steps shown therein are the same as the steps shown in and described above with reference to FIG. 6A, and thus, such steps are labeled the same and need not be described again. A comparison between FIGS. 6A and 6B shows that steps 601, 617, and 631 are added in FIG. 6B. At step 601 the invalid message count threshold (imct) is set to a first value, i.e., $imct_1$. Similarly, at step 617, after a valid message has been received and acted upon, the invalid message count threshold (imct) is set to the same first value, i.e., $imct_1$. By contrast, at step 631, the invalid message count threshold (imct) is set to a second value, i.e., $imct_2$. In accordance with certain embodiments, $imct_2$ is less than $imct_1$. As noted above, this method variant effectively makes it more difficult for the IMD to exit from a Noise State that the IMD enters during the disable period, assuming the IMD is configured to remain in the Noise State (once the Noise State is entered) until a valid message (or a specified number of valid messages) are thereafter received. The method variant described with reference to FIG. 6B provides for hysteresis and biases the method away from a premature exit from the Noise State, assuming the IMD is configured to remain in the Noise State (once the Noise State is entered) until a valid message (or a specified number of valid messages) are thereafter received.

In alternative embodiments, rather than modifying the invalid message count threshold (imct) based on whether a valid message was received during an immediately preceding message alert period, an amount by which the invalid message count is incremented (in response an invalid message being received) can be modified. For example, in accordance with an embodiment, an amount by which the invalid message count is incremented in response to determining that a message received during a message alert period is invalid, can be greater if a valid message was not detected during an immediately preceding message alert period, compared to if a valid message was detected during the immediately preceding message alert period. Other variations are also possible and within the scope of the embodiments of the present technology described herein.

In accordance with certain embodiments, the invalid message count threshold (imct) is modified based on temporal information about invalid messages that were received. For example, where two invalid messages are received within a specified relatively short time period (and thus, within in rapid succession), that can be interpreted as being indicative of being caused by excessive interference. Thus, when this occurs, the invalid message count threshold (e.g., referred to in steps 626 and 628 in FIG. 6A) can be reduced so that a decision to enter the disable period (and simultaneously a Noise State) can occur in response to receiving relatively view invalid message.

Alternatively, an amount by which the invalid message count is incremented (e.g., at step 624 in FIG. 6A) can be modified based on temporal information about invalid messages that were received. For example, where two invalid messages are received within a specified relatively short time period (and thus, in rapid succession), that can be interpreted as being indicative of being caused by excessive interference, as noted above. Thus, when this occurs, the amount by which the invalid message count is incremented (e.g., at instances of step 624 in FIG. 6A) can be increased so that a decision to enter the disable period (and simultaneously a Noise State) can occur in response to receiving relatively few invalid message.

Whenever an IMD enters a disable period, and then after exiting a disable period again enters another disable period without receiving a valid message therebetween, it can be assumed that the interference or other noise (that prevented at least one valid message from being received during a message alert period) has continued to persist. In other words, if no valid message is received for two or more consecutive message alert periods, then it is assumed that persistent interference or other noise exists. In accordance with certain embodiments, when there is persistent interference or other noise the length of the disable period can be progressively increased. For example, an initial disable period can be equal to 1 cardiac cycle (or 1 second). Then, if no valid message is detected during the next message alert period (that follows the initial disable period), then the second disable period can be 5 cardiac cycles (or 5 seconds). Thereafter, if no valid message is detected during the following message alert period, then the third disable period can be 10 cardiac cycles (or 10 seconds). The process of progressively increasing the length of the disable period might continue, up to a maximum number of cardiac cycles (or a maximum number of seconds), if there are more consecutive message alert periods during which no valid message is received. Once a valid message is detected it can be assumed that the interference or other noise has subsided, and the length of the disable period can be immediately returned to its initial length (e.g., 1 cardiac cycle, or 1 second). Alternatively, the length of the disable period can be gradually stepped down to its initial or minimum length, just in case the subsiding of the interference or other noise was only temporary. The stepped down progression of the disable period that occurs in the absence of interference or other noise can follow the same trajectory (in reverse) as followed when no valid messages were received in multiple consecutive message alert periods, or the stepped down progression can follow a different trajectory that might recover faster (or slower) than the stepped up progression.

The length of a disable period can depend on alternative or additional information. In accordance with certain embodiments, the disable period (or an initial disable period that can be increased based on receiving no valid messages in consecutive message alert periods) can be set based on the current operational mode of the IMD that is performing the method. In other words, a length of a disable period during which a communication capability of an IMD is disabled, in response to the invalid message count reaching the corresponding invalid message count threshold, can depend on which one of a plurality of operational modes the IMD is set to, and thus, operating in. For example: when the IMD is in its normal operation mode the disable period can be 5 cardiac cycles (or 5 seconds); when the IMD is in a magnetic resonance imaging (MRI) ready operational mode the disable period the disable period can be 300 cardiac cycles (or 300 seconds); and when the IMD is in an RF ablation ready operational mode the can be 100 cardiac cycles (or 100 seconds). These are just a few examples, which are not meant to be all encompassing, as there are other possible operational modes, and there are other possible lengths for the disable period. The reason for increasing the disable period when the IMD is in an MRI ready operational mode is that it is expected that once the IMD experiences interference due to an MRI system, that interference is likely to last quite a while before it subsides. Similarly, interference caused by an RF ablation system would likely occur for a while, but not likely as long as would occur due to an MRI system.

As noted above, in accordance with certain embodiments, during a disable period the device enters a Noise State, during which time the device operates in a safe pacing mode (e.g., VVI or VOO) that does not depend on i2i (or other) communication. In certain embodiments, once the device enters the Noise State, the device remains in the Noise State (during which time the device operates in a safe pacing mode) until a specified number (that is greater than or equal to one) of valid messages are received. Preferably, the specified number is between one and five, inclusively, but is not limited thereto. The period or mode during which the IMD determines whether to exit the Noise State can be referred to as the re-confirm period or the re-confirm mode. Such embodiments increase the probability that interference has subsided before the device transitions from the Noise State back, during which a safe pacing mode is used, to its normal state or pacing mode (e.g., DDD, DDI, VDD, VDI, or DOO).

Figure 7:
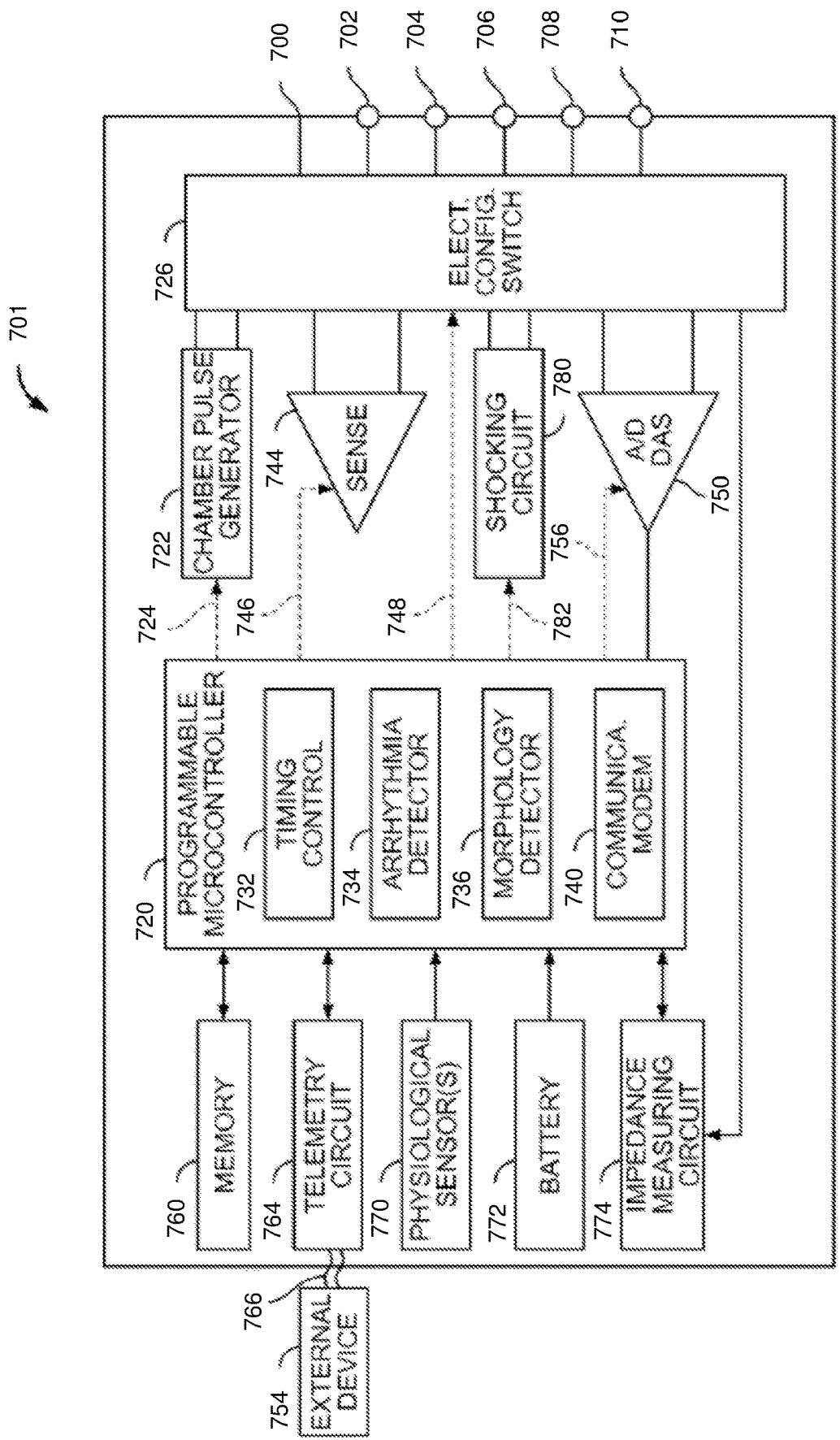
FIG. 7 shows a block diagram of one embodiment of an LP that is implanted into the patient as part of the implantable cardiac system in accordance with certain embodiments herein.

FIG. 7 shows a block diagram of one embodiment of an LP 701 that is implanted into the patient as part of the implantable cardiac system in accordance with certain embodiments herein. LP 701 may be implemented as a full-function biventricular pacemaker, equipped with both atrial and ventricular sensing and pacing circuitry for four chamber sensing and stimulation therapy (including both pacing and shock treatment). Optionally, LP 701 may provide full-function cardiac resynchronization therapy. Alternatively, LP 701 may be implemented with a reduced set of functions and components. For instance, the IMD may be implemented without ventricular sensing and pacing.

LP 701 has a housing 700 to hold the electronic/computing components. Housing 700 (which is often referred to as the "can", "case", "encasing", or "case electrode") may be programmably selected to act as the return electrode for certain stimulus modes. Housing 700 may further include a connector (not shown) with a plurality of terminals 702, 704, 706, 708, and 710. The terminals may be connected to electrodes that are located in various locations on housing 700 or elsewhere within and about the heart. LP 701 includes a programmable microcontroller 720 that controls various operations of LP 701, including cardiac monitoring and stimulation therapy. Microcontroller 720 includes a microprocessor (or equivalent control circuitry), RAM and/or ROM memory, logic and timing circuitry, state machine circuitry, and I/O circuitry.

LP 701 further includes a first pulse generator 722 that generates stimulation pulses for delivery by one or more electrodes coupled thereto. Pulse generator 722 is controlled by microcontroller 720 via control signal 724. Pulse generator 722 may be coupled to the select electrode(s) via an electrode configuration switch 726, which includes multiple switches for connecting the desired electrodes to the appropriate I/O circuits, thereby facilitating electrode programmability. Switch 726 is controlled by a control signal 728 from microcontroller 720.

In the embodiment of FIG. 7, a single pulse generator 722 is illustrated. Optionally, the IMD may include multiple pulse generators, similar to pulse generator 722, where each pulse generator is coupled to one or more electrodes and controlled by microcontroller 720 to deliver select stimulus pulse(s) to the corresponding one or more electrodes.

Microcontroller 720 is illustrated as including timing control circuitry 732 to control the timing of the stimulation pulses (e.g., pacing rate, atrioventricular (AV) delay, atrial interconduction (A-A) delay, or ventricular interconduction (V-V) delay, etc.). Timing control circuitry 732 may also be used for the timing of refractory periods, blanking intervals, noise detection windows, evoked response windows, alert intervals, marker channel timing, and so on. Microcontroller 720 also has an arrhythmia detector 734 for detecting arrhythmia conditions and a morphology detector 736. Although not shown, the microcontroller 720 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

LP 701 is further equipped with a communication modem (modulator/demodulator) 740 to enable wireless communication with the remote slave pacing unit. Modem 740 may include one or more transmitters and two or more receivers as discussed herein in connection with FIG. 1B. In one implementation, modem 740 may use low or high frequency modulation. As one example, modem 740 may transmit i2i messages and other signals through conductive communication between a pair of electrodes. Modem 740 may be implemented in hardware as part of microcontroller 720, or as software/firmware instructions programmed into and executed by microcontroller 720. Alternatively, modem 740 may reside separately from the microcontroller as a standalone component.

LP 701 includes a sensing circuit 744 selectively coupled to one or more electrodes, that perform sensing operations, through switch 726 to detect the presence of cardiac activity in the right chambers of the heart. Sensing circuit 744 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 726 determines the sensing polarity of the cardiac signal by selectively closing the appropriate switches. In this way, the clinician may program the sensing polarity independent of the stimulation polarity.

The output of sensing circuit 744 is connected to microcontroller 720 which, in turn, triggers or inhibits the pulse generator 722 in response to the presence or absence of cardiac activity. Sensing circuit 744 receives a control signal 746 from microcontroller 720 for purposes of controlling the gain, threshold, polarization charge removal circuitry (not shown), and the timing of any blocking circuitry (not shown) coupled to the inputs of the sensing circuitry.

In the embodiment of FIG. 7, a single sensing circuit 744 is illustrated. Optionally, the IMD may include multiple sensing circuits, similar to sensing circuit 744, where each sensing circuit is coupled to one or more electrodes and controlled by microcontroller 720 to sense electrical activity detected at the corresponding one or more electrodes. Sensing circuit 744 may operate in a unipolar sensing configuration or in a bipolar sensing configuration.

LP 701 further includes an analog-to-digital (ND) data acquisition system (DAS) 750 coupled to one or more electrodes via switch 726 to sample cardiac signals across any pair of desired electrodes. Data acquisition system 750 is configured to acquire intracardiac electrogram signals, convert the raw analog data into digital data, and store the digital data for later processing and/or telemetric transmission to an external device 754 (e.g., a programmer, local transceiver, or a diagnostic system analyzer). Data acquisition system 750 is controlled by a control signal 756 from the microcontroller 720.

Microcontroller 720 is coupled to a memory 760 by a suitable data/address bus. The programmable operating parameters used by microcontroller 720 are stored in memory 760 and used to customize the operation of LP 701 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 701 may be non-invasively programmed into memory 760 through a telemetry circuit 764 in telemetric communication via communication link 766 with external device 754. Telemetry circuit 764 allows intracardiac electrograms and status information relating to the operation of LP 701 (as contained in microcontroller 720 or memory 760) to be sent to external device 754 through communication link 766.

LP 701 can further include magnet detection circuitry (not shown), coupled to microcontroller 720, to detect when a magnet is placed over the unit. A magnet may be used by a clinician to perform various test functions of LP 701 and/or to signal microcontroller 720 that external device 754 is in place to receive or transmit data to microcontroller 720 through telemetry circuits 764.

LP 701 can further include one or more physiological sensors 770. Such sensors are commonly referred to as "rate-responsive" sensors because they are typically used to adjust pacing stimulation rates according to the exercise state of the patient. However, physiological sensor 770 may further be used to detect changes in cardiac output, changes in the physiological condition of the heart, or diurnal changes in activity (e.g., detecting sleep and wake states). Signals generated by physiological sensors 770 are passed to microcontroller 720 for analysis. Microcontroller 720 responds by adjusting the various pacing parameters (such as rate, AV Delay, V-V Delay, etc.) at which the atrial and ventricular pacing pulses are administered. While shown as being included within LP 701, physiological sensor(s) 770 may be external to LP 701, yet still be implanted within or carried by the patient. Examples of physiologic sensors might include sensors that, for example, sense respiration rate, pH of blood, ventricular gradient, activity, position/posture, minute ventilation (MV), and so forth.

A battery 772 provides operating power to all of the components in LP 701. Battery 772 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 772 also desirably has a predictable discharge characteristic so that elective replacement time can be detected. As one example, LP 701 employs lithium/silver vanadium oxide batteries.

LP 701 further includes an impedance measuring circuit 774, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 774 is coupled to switch 726 so that any desired electrode may be used. In this embodiment LP 701 further includes a shocking circuit 780 coupled to microcontroller 720 by a data/address bus 782.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology that are for use in reducing how often a first receiver of an IMD wakes up a second receiver of an IMD, in order to reduce power consumption, can also be used with other types of IMDs besides an LP. Accordingly, unless specifically limited to use with an LP, the claims should not be limited to use with LP type IMDs. For example, embodiments of the present technology can also be used with a subcutaneous-ICD and/or a subcutaneous pacemaker, but are not limited thereto.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 6A and 6B. For another example, it is possible to change the boundaries of some of the dashed blocks shown in FIGS. 2 and 7.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for use with an implantable medical device (IMD), the method comprising:
   during each message alert period of a plurality of message alert periods during which a communication capability of the IMD is enabled, determining whether a valid message is detected during the message alert period;
   temporarily disabling the communication capability of the IMD for a disable period, in response to determining that no valid message was detected during a said message alert period; and
   increasing a length of the disable period in response to no valid message being detected during two consecutive said message alert periods.

2. The method of claim 1, wherein:
   the increasing the length of the disable period, in response to no valid message being detected during two consecutive said message alert periods, comprises increasing the length of the disable period from a first number of cardiac cycles to a second number of cardiac cycles;
   the first number is one or greater; and
   the second number is greater than the first number.

3. The method of claim 1, wherein:
   the increasing the length of the disable period, in response to no valid message being detected during two consecutive said message alert periods, comprises increasing the length of the disable period from a first length of time to a second length of time that is longer than the first length of time.

4. The method of claim 1, further comprising:
   further increasing the length of the disable period in response to no valid message being detected during three consecutive message alert periods.

5. The method of claim 1, wherein:
   the communication capability of the IMD, which is temporarily disabled, comprises a communication capability related to at least one of a receiver or a transmitter of the IMD.

6. The method of claim 1, wherein:
   the IMD includes both a first receiver and a second receiver, wherein the first receiver is used to selectively wakeup the second receiver, and wherein the communication capability of the IMD, which is temporarily disabled, comprises a communication capability related to the first receiver.

7. The method of claim 1, wherein the IMD comprises a first leadless pacemaker (LP1) that is configured to communicate with a second leadless pacemaker (LP2) so that the LP1 and the LP2 can deliver synchronized therapy.

8. A method for use with an implantable medical device (IMD), the method comprising:
   during each message alert period of a plurality of message alert periods during which a communication capability of the IMD is enabled, determining whether a valid message is detected during the message alert period; and
   temporarily disabling the communication capability of the IMD for a disable period, in response to determining that no valid message was detected during a said message alert period;
   wherein a length of the disable period is dependent on an operational mode of the IMD, such that the length of the disable period when the IMD is operating in a first operational mode differs from the length of the disable period when the IMD is operating in a second operational mode.

9. The method of claim 8, wherein:
the first operational mode comprises a normal operational mode of the IMD;
the second operational mode comprises a magnetic resonance imaging (MRI) ready operational mode; and
the length of the disable period when the IMD is operating in the MRI ready operational mode is longer than the disable period when the IMD is operating in the normal operational mode.

10. The method of claim 8, wherein:
the length of the disable period when the IMD is operating in the first operational mode comprises a first length of time or a first number of cardiac cycles;
the length of the disable period when the IMD is operating in the second operational mode, which is greater than the length of the disable period when the IMD is operating in the first operational mode, comprises a second length of time or a second number of cardiac cycles; and
the length of the disable period when the IMD is operating in a third operational mode, which is greater than the length of the disable period when the IMD is operating in the second operational mode, comprises a third length of time or a third number of cardiac cycles.

11. The method of claim 10, wherein:
the first operational mode comprises a normal operational mode of the IMD;
the second operational mode comprises a magnetic resonance imaging (MRI) ready operational mode; and
the third operational mode comprises a radio frequency (RF) ablation ready operational mode.

12. The method of claim 8, wherein:
the communication capability of the IMD, which is temporarily disabled, comprises a communication capability related to at least one of a receiver or a transmitter of the IMD.

13. The method of claim 8, wherein:
the IMD includes both a first receiver and a second receiver, wherein the first receiver is used to selectively wakeup the second receiver, and wherein the communication capability of the IMD, which is temporarily disabled, comprises a communication capability related to the first receiver.

14. The method of claim 8, wherein the IMD comprises a first leadless pacemaker (LP1) that is configured to communicate with a second leadless pacemaker (LP2) so that the LP1 and the LP2 can deliver synchronized therapy.

15. A method for use with an implantable medical device (IMD) that is configured to perform pacing therapy, the method comprising:
during each message alert period of a plurality of message alert periods during which a communication capability of the IMD is enabled, determining whether a valid message is detected during the message alert period;
in response to determining that no valid message was detected during a said message alert period, temporarily disabling the communication capability of the IMD for a disable period and causing the IMD to enter a noise state during which a pacing mode of the IMD does not depend on communicating with another IMD; and
following the IMD entering into the noise state, maintaining the IMD in the noise state until a specified number of valid messages are received by the IMD.

16. The method of claim 15, further comprising:
causing the IMD to exit the noise state, in response to determining that the specified number of valid message were received by the IMD while the IMD was in the noise state.

17. The method of claim 15, further comprising:
pacing in accordance with one of a DDD, DDI, VDD, VDI, or DOO mode when the IMD is not in the noise state; and
pacing in accordance with one of a VVI or VOO mode when the IMD is in the noise state.

18. The method of claim 15, wherein:
the communication capability of the IMD, which is temporarily disabled, comprises a communication capability related to at least one of a receiver or a transmitter of the IMD.

19. The method of claim 15, wherein:
the IMD includes both a first receiver and a second receiver, wherein the first receiver is used to selectively wakeup the second receiver, and wherein the communication capability of the IMD, which is temporarily disabled, comprises a communication capability related to the first receiver.

20. The method of claim 15, wherein the IMD comprises a first leadless pacemaker (LP1) that is configured to communicate with a second leadless pacemaker (LP2) so that the LP1 and the LP2 can deliver synchronized therapy, and wherein the other IMD comprises the LP2.

* * * * *